(12) United States Patent
Boone et al.

(10) Patent No.: US 8,119,748 B2
(45) Date of Patent: Feb. 21, 2012

(54) HIGH ACTIVITY, LOW MOLECULAR WEIGHT OLEFIN POLYMERIZATION PROCESS

(75) Inventors: Harold W. Boone, Sugar Land, TX (US); Kevin A. Frazier, Midland, MI (US); Daniel D. VanderLende, Sugar Land, TX (US); Paul C. Vosejpka, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 764 days.

(21) Appl. No.: 12/088,108

(22) PCT Filed: Sep. 8, 2006

(86) PCT No.: PCT/US2006/035082
§ 371 (c)(1),
(2), (4) Date: Mar. 26, 2008

(87) PCT Pub. No.: WO2007/037944
PCT Pub. Date: Apr. 5, 2007

(65) Prior Publication Data
US 2008/0255329 A1    Oct. 16, 2008

Related U.S. Application Data

(60) Provisional application No. 60/721,295, filed on Sep. 28, 2005.

(51) Int. Cl.
*C08F 4/76* (2006.01)
*C08F 4/64* (2006.01)

(52) U.S. Cl. ........ 526/172; 526/161; 526/348; 526/352; 526/351; 526/905

(58) Field of Classification Search .......... 526/352, 526/348, 172, 161
See application file for complete search history.

(56) References Cited

U.S. PATENT DOCUMENTS

| | | | |
|---|---|---|---|
| 6,103,657 A | 8/2000 | Murray | |
| 6,906,160 B2 | 6/2005 | Stevens et al. | |
| 6,919,407 B2 | 7/2005 | Tau et al. | |
| 6,927,256 B2 | 8/2005 | Stevens et al. | |
| 7,524,913 B2 * | 4/2009 | Briggs et al. | 526/348.4 |
| 2002/0142912 A1 | 10/2002 | Boussie et al. | |
| 2004/0005984 A1 | 1/2004 | Boussie et al. | |
| 2004/0220050 A1 | 11/2004 | Frazier et al. | |
| 2009/0105407 A1 * | 4/2009 | Karjala et al. | 524/547 |

FOREIGN PATENT DOCUMENTS

| | | |
|---|---|---|
| WO | WO-0020377 | 4/2000 |
| WO | WO-0238628 | 5/2002 |
| WO | WO-2004026925 A1 | 4/2004 |
| WO | WO-2006022806 A1 | 3/2006 |

OTHER PUBLICATIONS

Dow Global Technologies, Inc., PCT/US2006/035082, International Preliminary Report on Patentability issued Apr. 1, 2008.
Dow Global Technologies, Inc., EP Appln. No. 06814361.9-1211, Rejection dated Nov. 14, 2008.
Dow Global Technologies, Inc., EP Appln. No. 06814361.9-1211, Response dated May 22, 2009.
Dow Global Technologies, Inc., EP Appln. No. 06814361.9-1211, Second Rejection dated Feb. 19, 2010.

* cited by examiner

*Primary Examiner* — Rip A. Lee

(57) ABSTRACT

Group 4 metal complexes comprising a polyvalent, heteroaryl donor ligand and their use as components of olefin polymerization catalysts, especially suited for preparing propylene/ethylene copolymer products having high isotacticity and low molecular weight, are disclosed.

4 Claims, No Drawings

HIGH ACTIVITY, LOW MOLECULAR WEIGHT OLEFIN POLYMERIZATION PROCESS

CROSS REFERENCE STATEMENT

This application claims the benefit of U.S. Provisional Application No. 60/721,295, filed Sep. 28, 2005.

BACKGROUND OF THE INVENTION

This invention relates to a Group 4 metal complex, to a catalyst composition and to a process for polymerizing addition polymerizable unsaturated monomers, especially olefins. In particular, the invention is directed to certain Group 4 metal complexes, to catalyst compositions comprising the same, and to addition polymerization processes using the same.

Advances in polymerization and catalysis have resulted in the capability to produce many new polymers having improved physical and chemical properties useful in a wide variety of superior products and applications. With the development of new catalysts the choice of polymerization-type (solution, slurry, high pressure or gas phase) for producing a particular polymer has been greatly expanded. Also, advances in polymerization technology have provided more efficient, highly productive and economically enhanced processes. Recently, several new disclosures related to metal complexes based on polyvalent metal-centered, heteroaryl donor ligands have published. Among these are U.S. Pat. Nos. 6,103,657, 6,906,160, 6,919,407, 6,927,256, US-A-2002/0142912, US-A-2004/0220050, US-A-2004/0005984, WO 2000/020377, and WO 2002/038628.

Regardless of the technological advances in the polyolefin industry afforded by this new class of catalyst, common problems, as well as new challenges associated with process operability, exist. For example, known Group 4 metal complexes based on donor ligands can produce extremely high molecular weight polymers, which in a solution polymerization can result in highly viscous reaction mixtures leading to high stirring forces and energy requirements. To decrease viscosity of the reaction mixture, higher polymerization temperatures may be employed. Disadvantageously however, higher reaction temperatures normally result in a reduction in polymer tacticity or crystallinity, especially when normally tactic, especially isotactic polymers, are produced. Alternatively, it is known to add a chain transfer agent such as hydrogen to the reactor to produce lower molecular weight polymers, thereby incidentally reducing polymer viscosity and ultimately, reaction mixture viscosity. Besides adding additional cost and complexity to the process, the solubility of standard chain transfer agents generally decreases at higher reaction temperatures thereby limiting their effectiveness. Additionally, the resulting polymers also tend to have broadened molecular weight distributions, rendering the product unsuited for some desired end uses.

Thus, it would be advantageous to provide a solution polymerization process for the polymerization of olefin monomers employing specific metal complexes based on donor ligands that are capable of operation at high temperatures and efficiencies and adapted to produce polymers having a desired molecular weight or melt flow while retaining the ability to control the molecular weight distribution of the resulting product. Moreover, it would be advantageous to provide a solution polymerization process for the polymerization of olefin monomers that is capable of operation at high temperatures and efficiencies and adapted to produce polymers having low molecular weights while using reduced quantities of chain transfer agent, especially hydrogen. Finally, it would be advantageous to provide a solution polymerization process for preparing tactic polymers, especially isotactic homopolymers and copolymers comprising propylene and/or a $C_{4-20}$ olefin that is capable of operation at high temperatures and adapted to produce polymers having a relatively low molecular weight while maintaining a relatively high tacticity or crystallinity, particularly one that does not require the use of excessive quantities of hydrogen or other chain transfer agent.

SUMMARY OF THE INVENTION

According to the present invention there is provided a Group 4 metal donor ligand complex for use as a catalyst component of an addition polymerization catalyst composition, said metal complex corresponding to the formula:

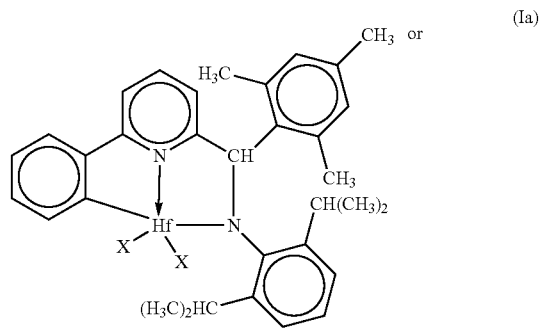

(Ia)

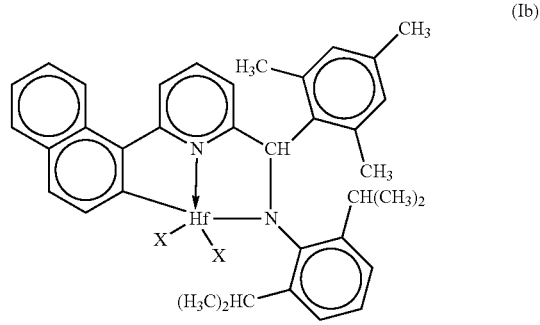

(Ib)

wherein, X is an anionic ligand group, preferably halo, alkyl, alkaryl, or trihydrocarbylsilylmethyl, more preferably chloro, methyl, n-butyl, benzyl, or tri(methyl)silylmethyl; and covalent bonds are represented by lines and coordination interactions are represented by arrows.

Additionally, according to the present invention there is provided a catalyst composition comprising one or more of the foregoing Group 4 metal complexes 1a or 1b and an activating cocatalyst capable of converting said metal complex into an active catalyst for addition polymerization. Additional components of such catalyst composition may include a carrier or support, a liquid solvent or diluent, a tertiary component such as a scavenger or secondary activator, and/or one or more additives or adjuvants such as processing aids, sequestrants, chain transfer agents, and/or chain shuttling agents.

In addition, the present invention provides an addition polymerizing process, especially an olefin polymerization process, wherein one or more addition polymerizable monomers are polymerized in the presence of the foregoing catalyst composition to form a high molecular weight polymer. Preferred polymerization processes are solution polymerizations, most preferably solution processes wherein ethylene, propylene, mixtures of ethylene and propylene, or mixtures of ethylene and/or propylene with one or more $C_{4-20}$ olefins or diolefins are polymerized or copolymerized. Desirably, the processes are capable of preparing polymers having improved melt flow properties while employing reduced quantities of hydrogen or other molecular weight control additives.

Highly desirably, the present invention provides a process wherein one or more addition polymerizable monomers are polymerized at a relatively high polymerization temperature in the presence of the foregoing catalyst composition to form a high molecular weight tactic polymer, especially a polymer that is isotactic or highly isotactic, and having a reduced molecular weight.

The metal complexes and catalysts of the invention may be used alone or combined with other metal complexes or catalyst compositions and the polymerization process may be used in series or in parallel with one or more other polymerization processes. Suitable additional polymerization catalyst compositions for use in combination with the metal complexes of the present invention include conventional Ziegler-Natta-type transition metal polymerization catalysts as well as π-bonded transition metal compounds such as metallocene-type catalysts, constrained geometry or other transition metal complexes, including other donor ligand complexes.

The catalysts of the invention are preferred for use as olefin polymerization catalysts because they are capable of producing polymers of relatively low molecular weight with either a relatively broad molecular weight distribution (for complexes of formula 1a) or a relatively narrow molecular weight distribution (for complexes of formula 1b) at higher reactor temperatures, while requiring reduced concentrations of hydrogen or other chain terminating agent in the reactor.

An additional advantage of the present invention is the ability to prepare propylene/ethylene- or propylene/ethylene/diene-interpolymers containing 85 percent or more polymerized propylene moieties and relatively low molecular weight (Mw) while retaining relatively high isotacticity as well as increased toughness. Another advantage is the ability to prepare propylene/ethylene interpolymers containing 65 percent or more polymerized propylene moieties and relatively low molecular weight (Mw) while retaining relatively high isotacticity. Using previously known catalysts, in order to produce such low molecular weight polymers higher levels of stereoerrors are necessarily introduced into the polymer, thereby reducing isotacticity and melting point (Tm) of the resulting polymer. The higher ethylene content polymers possess improved toughness, making them well suited for use in preparing fibers, especially by means of melt-blown or extrusion spinning processes. Moreover, the polymers are usefully employed in adhesive formulations or in multi-layer films and laminates demonstrating improved compatibility and adhesion to polyethylene substrates, layers or films.

DETAILED DESCRIPTION OF THE INVENTION

All reference to the Periodic Table of the Elements herein shall refer to the Periodic Table of the Elements, published and copyrighted by CRC Press, Inc., 2003. Unless stated to the contrary, clear from the context, or conventional in the art, all parts and percents are based on weight. Also, any reference to a Group or Groups shall be to the Group or Groups as reflected in this Periodic Table of the Elements using the IUPAC system for numbering groups.

The term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability. The term "consisting of" excludes any component, step or procedure not specifically delineated or listed. The term "or", unless stated otherwise, refers to the listed members individually as well as in any combination.

The term "hetero" or "hetero-atom" refers to a non-carbon atom, especially Si, B, N, P or O. "Heteroaryl", "heteroalkyl", "heterocycloalkyl" and "heteroaralkyl" refer to aryl, alkyl, cycloalkyl, or aralkyl groups respectively, in which at least one carbon atom is replaced by a heteroatom. "Inertly substituted" refers to substituents on a ligand that do not destroy operability of the invention. Preferred inert substituents are halo, di($C_{1-6}$ hydrocarbyl)amino, $C_{2-6}$ hydrocarbyleneamino, $C_{1-6}$ halohydrocarbyl, and tri($C_{1-6}$ hydrocarbyl)silyl. The term "polymer", as used herein, includes both homopolymers, that is, polymers prepared from a single reactive compound, and copolymers, that is, polymers prepared by reaction of at least two polymer forming reactive, monomeric compounds. The term "crystalline" refers to a polymer that exhibits an X-ray diffraction pattern at 25° C. and possesses a first order transition or crystalline melting point (Tm) from the differential scanning calorimetry heating curve. The term may be used interchangeably with the term "semicrystalline".

The term, "chain transfer agent" refers to a chemical substance that is able to transfer a growing polymer chain to all or a portion of the agent, thereby replacing the active catalyst site with a catalytically inactive species. By the term, "chain shuttling agent" is meant a chain transfer agent that is capable of returning the growing polymer chain back to the same or a different active catalyst site, wherein polymerization may resume. Thus, a chain shuttling agent is distinguished from a chain transfer agent in that polymer growth is not necessarily terminated due to interaction with said agent.

The invention is directed toward novel metal complexes and catalyst compositions comprising the same. The invention also relates to a polymerization process having improved operability and product capabilities using the present metal complexes in the specified catalyst composition. It has been surprisingly discovered that using the present catalyst composition results in a substantially reduced polymer molecular weight without the need to utilize excessive amounts of a chain transfer agent such as hydrogen. In particular, utilizing the present catalyst composition results in a substantial improvement in process operability, an ability to control polymer molecular weight without the use of chain terminating additives, the ability to prepare low molecular weight polymers having high tacticity or crystallinity, coupled with B-values from 1.03 to 1.09. The present invention thus gives the operator the capability to produce a broader range of polymers in a given reactor configuration.

As used herein, the term, "B value" refers to the measure of distribution (random or non-random) of monomer units in a copolymer, and is determined according to the technique of J. L. Koenig, "Spectroscopy of Polymers", American Chemical Society, pub., Washington, D.C., (1992). Specifically, the term may be used with regard to the polymerized ethylene units of a copolymer of propylene and ethylene or of a copolymer of propylene, ethylene and at least one unsaturated comonomer. B-values may range from 0 to 2. For copolymers having a higher B-value, the comonomer distribution is more alternating. For copolymers having a lower B-value, the comonomer distribution is more blocky or clustered. A B-value of 1.00 indicates a perfectly random copolymer.

Typically, the B-values of propylene/ethylene copolymers made using a non-metallocene, metal-centered, heteroaryl ligand catalyst, such as those described in U.S. Pat. No. 6,927,256, are greater than 1.00, and generally fall from 1.03-1.09, whereas the B-values of propylene/ethylene copolymers made using catalysts comprising π-bonded ligand group, such as metallocenes, are typically less than 1.00, and generally from 0.80 to 0.95.

The polymers of the invention also have substantially isotactic propylene sequences. "Substantially isotactic propylene sequences" and similar terms mean that the sequences have an isotactic triad (mm) measured by $^{13}$C NMR of greater than 0.85, preferably greater than 0.90, more preferably greater than 0.93 and most preferably greater than 0.95. Measurement of isotactic triads by the foregoing technique is known in the art and previously disclosed in U.S. Pat. No. 5,504,172, WO 00/01745 and elsewhere.

The previously described metal complexes according to the invention are typically activated in various ways to yield catalyst compounds having a vacant coordination site that will coordinate, insert, and polymerize addition polymerizable monomers, especially olefin(s). For the purposes of this patent specification and appended claims, the term "activator" or "cocatalyst" is defined to be any compound or component or method which can activate any of the catalyst compounds of the invention as described above. Non-limiting examples of suitable activators include Lewis acids, non-coordinating ionic activators, ionizing activators, organometal compounds, and combinations of the foregoing substances that can convert a neutral catalyst compound to a catalytically active species.

It is believed, without desiring to be bound by such belief, that in one embodiment of the invention, catalyst activation may involve formation of a cationic, partially cationic, or zwitterionic species, by means of proton transfer, oxidation, or other suitable activation process. It is to be understood that the present invention is operable and fully enabled regardless of whether or not such an identifiable cationic, partially cationic, or zwitterionic species actually results during the activation process, also interchangeably referred to herein as an "ionization" process or "ionic activation process".

One suitable class of organometal activators or cocatalysts are alumoxanes, also referred to as alkylaluminoxanes. Alumoxanes are well known activators for use with metallocene type catalyst compounds to prepare addition polymerization catalysts. There are a variety of methods for preparing alumoxanes and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451 5,744,656; European publications EP-A-561476, EP-A-279586 and EP-A-594218; and PCT publication WO 94/10180. Preferred alumoxanes are tri($C_{3-6}$)alkylalumunium modified methylalumoxane, especially tri(isobutyl)aluminum modified methylalumoxane, available commercially as MMAO-3A, from Akzo Nobel, Inc.

It is within the scope of this invention to use alumoxane(s) or modified alumoxane(s) as an activator or as a tertiary component in the invented process. That is, the compound may be used alone or in combination with other activators, neutral or ionic, such as tri(alkyl)ammonium tetrakis(pentafluorophenyl)borate compounds, trisperfluoroaryl compounds, polyhalogenated heteroborane anions (WO 98/43983), and combinations thereof. When used as a tertiary component, the amount of alumoxane employed is generally less than that necessary to effectively activate the metal complex when employed alone. In this embodiment, it is believed, without wishing to be bound by such belief, that the alumoxane does not contribute significantly to actual catalyst activation. Not withstanding the foregoing, it is to be understood that some participation of the alumoxane in the activation process is not necessarily excluded.

Ionizing cocatalysts may contain an active proton, or some other cation associated with, but not coordinated to or only loosely coordinated to, an anion of the ionizing compound. Such compounds are described in European publications EP-A-570982, EP-A-520732, EP-A-495375, EP-A-500944, EP-A-277 003 and EP-A-277004, and U.S. Pat. Nos. 5,153,157, 5,198,401, 5,066,741, 5,206,197, 5,241,025, 5,384,299 and 5,502,124. Preferred among the foregoing activators are ammonium cation containing salts, especially those containing trihydrocarbyl-substituted ammonium cations containing one or two $C_{10-40}$ alkyl groups, especially methylbis(octadecyl)ammonium- and methylbis(tetradecyl)-ammonium-cations and a non-coordinating anion, especially a tetrakis(perfluoro)arylborate anion, especially tetrakis (pentafluorophenyl)borate. It is further understood that the cation may comprise a mixture of hydrocarbyl groups of differing lengths. For example, the protonated ammonium cation derived from the commercially available long-chain amine comprising a mixture of two $C_{14}$, $C_{16}$ or $C_{18}$ alkyl groups and one methyl group. Such amines are available from Chemtura Corp., under the trade name Kemamine™ T9701, and from Akzo-Nobel under the trade name Armeen™ M2HT. A most preferred ammonium salt activator is methyldi ($C_{14-20}$alkyl)ammonium tetrakis(pentafluorophenyl)borate.

Activation methods using ionizing ionic compounds not containing an active proton but capable of forming active catalyst compositions, such as ferrocenium salts of the foregoing non-coordinating anions are also contemplated for use herein, and are described in EP-A-426637, EP-A-573403 and U.S. Pat. No. 5,387,568.

A class of cocatalysts comprising non-coordinating anions generically referred to as expanded anions, further disclosed in U.S. Pat. No. 6,395,671, may be suitably employed to activate the metal complexes of the present invention for olefin polymerization. Generally, these cocatalysts (illustrated by those having imidazolide, substituted imidazolide, imidazolinide, substituted imidazolinide, benzimidazolide, or substituted benzimidazolide anions) may be depicted as follows:

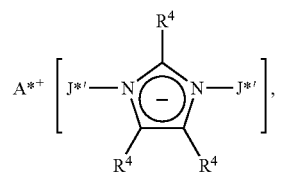

-continued

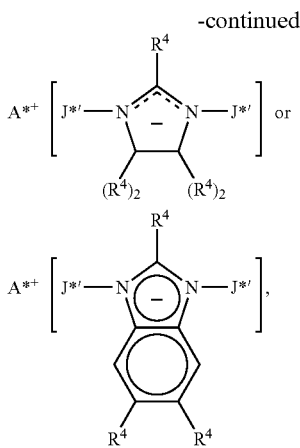

wherein:

A*+ is a cation, especially a proton containing cation, and preferably is a trihydrocarbyl ammonium cation containing one or two $C_{10-40}$ alkyl groups, especially a methyldi($C_{14-20}$alkyl)ammonium-cation, $R^4$, independently each occurrence, is hydrogen or a halo, hydrocarbyl, halocarbyl, halohydrocarbyl, silylhydrocarbyl, or silyl, (including mono-, di- and tri(hydrocarbyl)silyl) group of up to 30 atoms not counting hydrogen, preferably $C_{1-20}$ alkyl, and J*' is tris(pentafluorophenyl)borane or tris(pentafluorophenyl)alumane).

Examples of these catalyst activators include trihydrocarbylammoniumn-salts, especially, methyldi($C_{14-20}$alkyl)ammonium-salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide,
bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl)alumane)imidazolide,
bis(tris(pentafluorophenyl)alumane)-2-undecylimidazolide,
bis(tris(pentafluorophenyl)alumane)-2-heptadecylimidazolide,
bis(tris(pentafluorophenyl)alumane)-4,5-bis(undecyl)imidazolide,
bis(tris(pentafluorophenyl)alumane)-4,5-bis(heptadecyl) imidazolide,
bis(tris(pentafluorophenyl)alumane)imidazolinide,
bis(tris(pentafluorophenyl)alumane)-2-undecylimidazolinide,
bis(tris(pentafluorophenyl)alumane)-2-heptadecylimidazolinide,
bis(tris(pentafluorophenyl)alumane)-4,5-bis(undecyl)imidazolinide,
bis(tris(pentafluorophenyl)alumane)-4,5-bis(heptadecyl) imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

Other activators include those described in PCT publication WO 98/07515 such as tris(2,2',2"-nonafluorobiphenyl) fluoroaluminate. Combinations of activators are also contemplated by the invention, for example, alumoxanes and ionizing activators in combinations, see for example, EP-A-0 573120, PCT publications WO 94/07928 and WO 95/14044 and U.S. Pat. Nos. 5,153,157 and 5,453,410. WO 98/09996 describes activating catalyst compounds with perchlorates, periodates and iodates, including their hydrates. WO 99/18135 describes the use of organoboroaluminum activators. EP-A-781299 describes using a silylium salt in combination with a non-coordinating compatible anion. Other activators or methods for activating a catalyst compound are described in for example, U.S. Pat. Nos. 5,849,852, 5,859, 653, 5,869,723, EP-A-615981, and PCT publication WO 98/32775.

It is also within the scope of this invention that the above described metal complexes can be combined with more than one of the activators or activation methods described above. The mole ratio of the activator component(s) to the metal complex in the catalyst compositions of the invention suitably is in the range of between 0.3:1 to 2000:1, preferably 1:1 to 800:1, and most preferably 1:1 to 500:1. Where the activator is an ionizing activator such as those based on the anion tetrakis(pentafluorophenyl)boron or the strong Lewis acid trispentafluorophenylboron, the mole ratio of the metal or metalloid of the activator component to the metal complex is preferably in the range of between 0.3:1 to 3:1.

Tertiary Components

In addition to the metal complex and cocatalyst or activator, it is contemplated that certain tertiary components or mixtures thereof may be added to the catalyst composition or the reaction mixture in order to obtain improved catalyst performance or other benefit. Examples of such tertiary components include scavengers designed to react with contaminants in the reaction mixture to prevent catalyst deactivation. Suitable tertiary components may also activate or assist in activation of one or more of the metal complexes employed in the catalyst composition.

Examples include Lewis acids, such as trialkylaluminum compounds, dialkylzinc compounds, dialkylaluminumalkoxides, dialkylaluminumaryloxides, dialkylaluminum N,N-dialkylamides, di(trialkylsilyl)aluminum N,N-dialkylamides, dialkylaluminum N,N-di(trialkylsilyl)amides, alkylaluminumdialkoxides, alkylaluminum di(N,N-dialkylamides), tri(alkyl)silylaluminum N,N-dialkylamides, alkylaluminum N,N-di(trialkylsilyl)amides, alkylaluminum diaryloxides, alkylaluminum µ-bridged bis(amides) such as bis(ethylaluminum)-1-phenylene-2-(phenyl)amido µ-bis(diphenylamide), and/or alumoxanes, as well as Lewis bases, such as organic ether, polyether, amine, and polyamine compounds. Many of the foregoing compounds and their use in polymerizations is disclosed in U.S. Pat. Nos. 5,712,352 and 5,763, 543, and in WO 96/08520. Preferred examples of the foregoing tertiary components include trialkylaluminum compounds, dialkylaluminum aryloxides, alkylaluminum diaryloxides, dialkylaluminum amides, alkylaluminum diamides, dialkylaluminum tri(hydrocarbylsilyl)amides, alkylaluminum bis(tri(hydrocarbylsilyl)amides), alumoxanes, and modified alumoxanes. Highly preferred tertiary components are alumoxanes, modified alumoxanes, or compounds corresponding to the formula $R^e{}_2Al(OR^f)$ or $R^e{}_2Al(NR^g{}_2)$ wherein $R^e$ is $C_{1-20}$ alkyl, $R^f$ independently each occurrence is $C_{6-20}$ aryl, preferably phenyl or 2,6-di-t-butyl-4-methylphenyl, and $R^g$ is $C_{1-4}$ alkyl or tri($C_{1-4}$alkyl)silyl, preferably trimethylsilyl. Most highly preferred tertiary components include methylalumoxane, tri(isobutylaluminum)-modified methylalumoxane, di(n-octyl)aluminum 2,6-di-t-butyl-4-methylphenoxide, and di(2-methylpropyl)aluminum N,N-bis(trimethylsilyl)amide.

Another example of a suitable tertiary component is a hydroxycarboxylate metal salt, by which is meant any hydroxy-substituted, mono-, di- or tri-carboxylic acid salt wherein the metal portion is a cationic derivative of a metal from Groups 1-13 of the Periodic Table of Elements. This compound may be used to improve polymer morphology especially in a gas phase polymerization. Non-limiting examples include saturated, unsaturated, aliphatic, aromatic or saturated cyclic, substituted carboxylic acid salts where the carboxylate ligand has from one to three hydroxy substituents and from 1 to 24 carbon atoms. Examples include hydroxyacetate, hydroxypropionate, hydroxybutyrate, hydroxyvalerate, hydroxypivalate, hydroxycaproate, hydroxycaprylate, hydroxyheptanate, hydroxypelargonate, hydroxyundecanoate, hydroxyoleate, hydroxyoctoate, hydroxyalmitate, hydroxymyristate, hydroxymargarate, hydroxystearate, hydroxyarachate and hydroxytercosanoate. Non-limiting examples of the metal portion includes a metal selected from the group consisting of Al, Mg, Ca, Sr, Sn, Ti, V, Ba, Zn, Cd, Hg, Mn, Fe, Co, Ni, Pd, Li and Na. Preferred metal salts are zinc salts.

In one embodiment, the hydroxycarboxylate metal salt is represented by the following general formula:

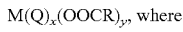

$M(Q)_x(OOCR)_y$, where

M is a metal from Groups 1 to 16 and the Lanthanide and Actinide series, preferably from Groups 1 to 7 and 12 to 16, more preferably from Groups 3 to 7 and 12 to 14, even more preferably Group 12, and most preferably Zn;

Q is halogen, hydrogen, hydroxide, or an alkyl, alkoxy, aryloxy, siloxy, silane, sulfonate or siloxane group of up to 20 atoms not counting hydrogen;

R is a hydrocarbyl radical having from 1 to 50 carbon atoms, preferably 1 to 20 carbon atoms, and optionally substituted with one or more hydroxy, alkoxy, N,N-dihydrocarbylamino, or halo groups, with the proviso that in one occurrence R is substituted with a hydroxy- or N,N-dihydrocarbylamino-group, preferably a hydroxy-group that is coordinated to the metal, M by means of unshared electrons thereof;

x is an integer from 0 to 3;

y is an integer from 1 to 4.

In a preferred embodiment M is Zn, x is 0 and y is 2.

Preferred examples of the foregoing hydroxycarboxylate metal salts include compounds of the formulas:

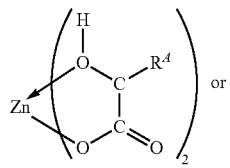 or

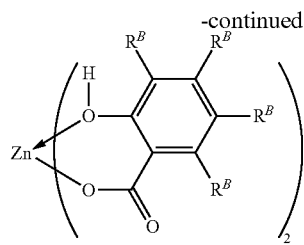

wherein $R^A$ and $R^B$ independently each occurrence are hydrogen, halogen, or $C_{1-6}$ alkyl.

Other additives may be incorporated into the catalyst compositions or employed simultaneously in the polymerization reaction for one or more beneficial purposes. Examples of additives that are known in the art include metal salts of fatty acids, such as aluminum, zinc, calcium, titanium or magnesium mono, di- and tri-stearates, octoates, oleates and cyclohexylbutyrates. Examples of such additives include Aluminum Stearate #18, Aluminum Stearate #22, Aluminum Stearate #132 and Aluminum Stearate EA Food Grade, all of which are available from Chemtura Corp. The use of such additives in a catalyst composition is disclosed in U.S. Pat. No. 6,306,984.

Additional suitable additives include antistatic agents such as fatty amines, for example, AS 990 ethoxylated stearyl amine, AS 990/2 zinc additive, a blend of ethoxylated stearyl amine and zinc stearate, or AS 990/3, a blend of ethoxylated stearyl amine, zinc stearate, and octadecyl-3,5-di-tert-butyl-4-hydroxyhydrocinnamate, also available from Chemtura Corp.

The above described catalyst compounds and catalyst compositions may be combined with one or more support materials or carriers using one of the support methods well known in the art or as described below. Such supported catalysts are particularly useful for slurry or gas phase polymerizations. Either the catalyst composition or the individual components thereof may be in a supported form, for example deposited on, contacted with, or incorporated within a support or carrier.

The terms "support" or "carrier" are used interchangeably and are any porous or non-porous support material, preferably a porous support material, for example, inorganic oxides, carbides, nitrides, and halides. Other carriers include resinous support materials such as polystyrene, a functionalized or crosslinked organic supports, such as polystyrene divinyl benzene polyolefins or polymeric compounds, or any other organic or inorganic support material, or mixtures thereof.

The preferred carriers are inorganic oxides that include those Group 2, 3, 4, 5, 13 or 14 metal oxides. The preferred supports include silica, alumina, silica-alumina, silicon carbide, boron nitride, and mixtures thereof. Other useful supports include magnesia, titania, zirconia, and clays. Also, combinations of these support materials may be used, for example, silica-chromium and silica-titania.

It is preferred that the carrier has a surface area in the range of from 10 to 700 m²/g, pore volume in the range of from 0.1 to 4.0 cc/g and average particle size in the range of from 10 to 500 μm. More preferably, the surface area of the carrier is in the range of from 50 to 500 m²/g, pore volume of from 0.5 to 3.5 cc/g, and average particle size of from 20 to 200 μm. Most preferably the surface area of the carrier is in the range of from 100 to 400 m²/g, pore volume from 0.8 to 3.0 cc/g and average particle size is from 20 to 100 μm. The average pore size of a carrier of the invention is typically in the range of from 1 to 100 nm, preferably 5 to 50 nm, and most preferably 7.5 to 35 nm.

Examples of supported catalyst compositions suitably employed in the present invention are described in U.S. Pat. Nos. 4,701,432, 4,808,561, 4,912,075, 4,925,821, 4,937,217, 5,008,228, 5,238,892, 5,240,894, 5,332,706, 5,346,925, 5,422,325, 5,466,649, 5,466,766, 5,468,702, 5,529,965, 5,554,704, 5,629,253, 5,639,835, 5,625,015, 5,643,847, 5,665,665, 5,698,487, 5,714,424, 5,723,400, 5,723,402, 5,731,261, 5,759,940, 5,767,032 and 5,770,664; and PCT publications WO 95/32995, WO 95/14044, WO 96/06187 and WO 97/02297.

Examples of techniques for supporting conventional-type catalyst compositions that may also be employed in the present invention are described in U.S. Pat. Nos. 4,894,424, 4,376,062, 4,395,359, 4,379,759, 4,405,495 4,540758 and 5,096,869. It is contemplated that the catalyst compounds of the invention may be deposited on the same support together with an activator, or that the activator may be used in an unsupported form, or deposited on a support different from the supported catalyst compounds of the invention, or any combination thereof.

There are various other methods in the art for supporting a polymerization catalyst compound or catalyst compositions suitable for use in the present invention. For example, the catalyst compound of the invention may contain a polymer bound ligand as described in U.S. Pat. Nos. 5,473,202 and 5,770,755. The catalyst composition of the present invention may also be spray dried using techniques as described in U.S. Pat. No. 5,648,310. The support used with the catalyst composition of the invention may be functionalized as described in European publication EP-A-802 203. At least one substituent or leaving group of the catalyst may be selected as described in U.S. Pat. No. 5,688,880. The supported catalyst composition may include a surface modifier as described in WO 96/11960.

A preferred method for producing a supported catalyst composition according to the invention is described in PCT publications WO 96/00245 and WO 96/00243. In this preferred method, the catalyst compound and activators are combined in separate liquids. The liquids may be any compatible solvent or other liquid capable of forming a solution or slurry with the catalyst compounds and/or activator. In the most preferred embodiment the liquids are the same linear or cyclic aliphatic or aromatic hydrocarbon, most preferably hexane or toluene. The catalyst compound and activator mixtures or solutions are mixed together and optionally added to a porous support or, alternatively, the porous support is added to the respective mixtures. The resulting supported composition may be dried to remove diluent, if desired, or utilized separately or in combination in a polymerization. Highly desirably the total volume of the catalyst compound solution and the activator solution or the mixtures thereof is less than five times the pore volume of the porous support, more preferably less than four times, even more preferably less than three times; with most prefer ranges being from 1.1 times to 3.5 times the pore volume of the support.

Procedures for measuring the total pore volume of a porous support are well known in the art. The preferred procedure is BET nitrogen absorption. Another suitable method well known in the art is described in Innes, Total Porosity and Particle Density of Fluid Catalysts By Liquid Titration, *Analytical Chemistry*, (1956) 28, 332-334.

It is further contemplated by the invention that other catalysts can be combined with the catalyst compounds of the invention. Examples of such other catalysts are disclosed in U.S. Pat. Nos. 4,937,299, 4,935,474, 5,281,679, 5,359,015, 5,470,811, 5,719,241, 4,159,965, 4,325,837, 4,701,432, 5,124,418, 5,077,255, 5,183,867, 5,391,660, 5,395,810, 5,691,264, 5,723,399 and 5,767,031; and PCT Publication WO 96/23010. In particular, the compounds that may be combined with the metal complexes of the invention to produce mixtures of polymers in one embodiment of the invention include conventional Ziegler-Natta transition metal compounds as well as coordination complexes, including transition metal complexes.

Conventional Ziegler-Natta transition metal compounds include the well known magnesium dichloride supported compounds, vanadium compounds, and chromium catalysts (also known as "Phillips type catalysts"). Examples of these catalysts are discussed in U.S. Pat. Nos. 4,115,639, 4,077,904 4,482,687, 4,564,605, 4,721,763, 4,879,359 and 4,960,741. Suitable transition metal complexes that may be used in the present invention include transition metal compounds from Groups 3 to 8, preferably Group 4 of the Periodic Table of Elements containing inert ligand groups and capable of activation by contact with a cocatalyst.

Suitable Ziegler-Natta catalyst compounds include alkoxy, phenoxy, bromide, chloride and fluoride derivatives of the foregoing metals, especially titanium. Preferred titanium compounds include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3.\frac{1}{3}AlCl_3$ and $Ti(OC_{12}H_{25})Cl_3$, and mixtures thereof, preferably supported on an inert support, usually $MgCl_2$. Other examples are described in, U.S. Pat. Nos. 4,302,565, 4,302,566, and 6,124,507, for example.

Non-limiting examples of vanadium catalyst compounds include vanadyl trihalide, alkoxy halides and alkoxides such as $VOCl_3$, $VOCl_2(OBu)$ where Bu is butyl and $VO(OC_2H_5)_3$; vanadium tetra-halide and vanadium alkoxy halides such as $VCl_4$ and $VCl_3(OBu)$; vanadium and vanadyl acetyl acetonates and chloroacetyl acetonates such as $V(AcAc)_3$ and $VOCl_2(AcAc)$ where (AcAc) is an acetyl acetonate.

Conventional-type chromium catalyst compounds suitable for use in the present invention include $CrO_3$, chromocene, silyl chromate, chromyl chloride ($CrO_2Cl_2$), chromium-2-ethyl-hexanoate, and chromium acetylacetonate ($Cr(AcAc)_3$). Non-limiting examples are disclosed in U.S. Pat. Nos. 2,285,721, 3,242,099 and 3,231,550.

Still other conventional-type transition metal catalyst compounds suitable for use in the present invention are disclosed in U.S. Pat. Nos. 4,124,532, 4,302,565, 4,302,566 and 5,763,723 and EP-A-416815 and EP-A-420436.

Cocatalyst compounds for use with the above conventional-type catalyst compounds are typically organometallic derivatives of metals of Groups 1, 2, 12 or 13. Non-limiting examples include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, aluminum trialkyl compounds, such as tri-hexylaluminum, triethylaluminum, trimethylaluminum, and tri-isobutylaluminum. Other suitable cocatalyst compounds include mono-organohalides and hydrides of Group 13 metals, and mono- or di-organohalides and hydrides of Group 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, dibromoaluminum hydride and bromocadmium hydride. Conventional-type organometallic cocatalyst compounds are known to those in the art and a more complete discussion of these compounds may be found in U.S. Pat. Nos. 3,221,002 and 5,093,415.

Suitable transition metal coordination complexes include metallocene catalyst compounds, which are half and full sandwich compounds having one or more π-bonded ligands including cyclopentadienyl-type structures or other similar functioning structure such as pentadiene, cyclooctatetraendiyl and imides. Typical compounds are generally described as coordination complexes containing one or more ligands capable of π-bonding to a transition metal atom, usually, cyclopentadienyl derived ligands or moieties, in combination with a transition metal selected from Group 3 to 8, preferably 4, 5 or 6 or from the lanthanide and actinide series of the Periodic Table of Elements. Exemplary of metallocene-type catalyst compounds are described in, for example, U.S. Pat. Nos. 4,530,914, 4,871,705, 4,937,299, 5,017,714, 5,055,438, 5,096,867, 5,120,867, 5,124,418, 5,198,401, 5,210,352, 5,229,478, 5,264,405, 5,278,264, 5,278,119, 5,304,614, 5,324,800, 5,347,025, 5,350,723, 5,384,299, 5,391,790, 5,391,789, 5,399,636, 5,408,017, 5,491,207, 5,455,366, 5,534,473, 5,539,124, 5,554,775, 5,621,126, 5,684,098, 5,693,730, 5,698,634, 5,710,297, 5,712,354, 5,714,427, 5,714,555, 5,728,641, 5,728,839, 5,753,577, 5,767,209, 5,770,753 and 5,770,664; European publications: EP-A-0 591 756, EP-A-0 520 732, EP-A-0 420 436, EP-A-0 485 822, EP-A-0 485 823, EP-A-0 743 324, EP-A-0 518 092; and PCT publications: WO 91/04257, WO 97/19959, WO 97/46567, WO 98/01455, WO 98/06759 and WO 98/011144.

Preferred examples of metallocenes used in combination with the metal complexes of the present invention include compounds of the formulas:

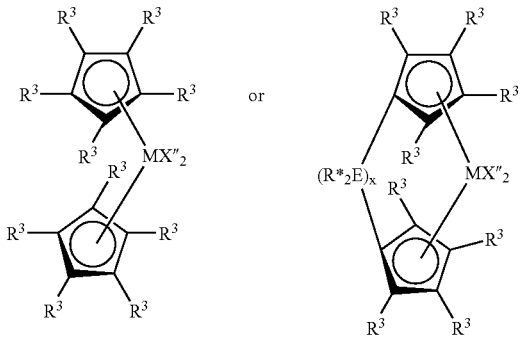

wherein:

M is titanium, zirconium or hafnium, preferably zirconium or hafnium, in the +2 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused-ring system, X" independently each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms forming a π-complex with M, whereupon M is in the +2 formal oxidation state;

R* independently each occurrence is $C_{1-4}$ alkyl or phenyl,

E independently each occurrence is carbon or silicon, and x is an integer from 1 to 8.

Additional examples of coordination complexes used in combination with the metal complexes of the present invention are those of the formula:

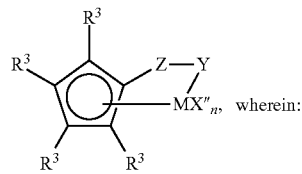

M is titanium, zirconium or hafnium in the +2, +3 or +4 formal oxidation state;

$R^3$ in each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused-ring system, each X" is a halo, hydrocarbyl, hydrocarbyloxy, hydrocarbylamino, or silyl group, said group having up to 20 non-hydrogen atoms, or two X" groups together form a neutral $C_{5-30}$ conjugated diene or a divalent derivative thereof;

Y is —O—, —S—, —NR*—, —PR*—;

Z is $SiR^*_2$, $CR^*_2$, $SiR^*_2SiR^*_2$, $CR^*_2CR^*_2$, $CR^*=CR^*$, $CR^*_2SiR^*_2$, or $GeR^*_2$, wherein R* is as previously defined, and n is an integer from 1 to 3.

The foregoing types of coordination complexes are described in, for example, U.S. Pat. Nos. 5,703,187, 5,965,756, 6,150,297, 5,064,802, 5,145,819, 5,149,819, 5,243,001, 5,239,022, 5,276,208, 5,296,434, 5,321,106, 5,329,031, 5,304,614, 5,677,401 and 5,723,398, PCT publications WO 93/08221, WO 93/08199, WO 95/07140, WO 98/11144, WO02/02577, WO 02/38628; and European publications EP-A-578838, EP-A-638595, EP-A-513380 and EP-A-8 16372.

Additional suitable metal coordination complexes used in combination with the metal complexes of the present invention are complexes of a transition metal, a substituted or unsubstituted π-bonded ligand, and one or more heteroallyl moieties, such as those described in U.S. Pat. Nos. 5,527,752 and 5,747,406, and EP-B-0 735 057. Preferably, these catalyst compounds are represented by one of the following formulas:

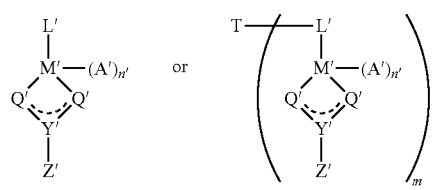

wherein M' is a metal from Groups 4, 5 or 6 or the Periodic Table of the Elements, preferably titanium, zirconium or hafnium, most preferably zirconium or hafnium;

L' is a substituted or unsubstituted, π-bonded ligand coordinated to M' and, when T is present, bonded to T, preferably L' is a cycloalkadienyl ligand, optionally with one or more hydrocarbyl substituent groups having from 1 to 20 carbon atoms, or fused-ring derivatives thereof, for example, a cyclopentadienyl, indenyl or fluorenyl ligand;

each Q' is independently selected from the group consisting of —O—, —NR'—, —CR'$_2$— and —S—, preferably oxygen;

Y' is either C or S, preferably carbon;

Z' is selected from the group consisting of —OR', —NR'$_2$, —CR'$_3$, —SR', —SiR'$_3$, —PR'$_2$, —H, and substituted or unsubstituted aryl groups, with the proviso that when Q is —NR'— then Z is selected from the group consisting of: —OR', —NR'$_2$, —SR', —SiR'$_3$, —PR'$_2$ and —H, preferably Z is selected from the group consisting of —OR', —CR'$_3$ and —NR'$_2$;

n' is 1 or 2, preferably 1;

A' is a univalent anionic group when n is 2 or A' is a divalent anionic group when n is 1, preferably A' is a carbamate, hydroxycarboxylate, or other heteroallyl moiety described by the Q', Y' and Z' combination;

each R' is independently a group containing carbon, silicon, nitrogen, oxygen, and/or phosphorus and one or more R' groups may be also attached to the L' substituent, preferably R' is a hydrocarbon group containing from 1 to 20 carbon atoms, most preferably an alkyl, cycloalkyl, or an aryl group;

T is a bridging group selected from the group consisting of alkylene and arylene groups containing from 1 to 10 carbon atoms optionally substituted with carbon or heteroatom(s), germanium, silicon and alkyl phosphine; and m is 2 to 7, preferably 2 to 6, most preferably 2 or 3.

In the foregoing formulas, the supportive substituent formed by Q', Y' and Z' is a uncharged polydentate ligand exerting electronic effects due to its high polarizability, similar to the cyclopentadienyl ligand. In the most referred embodiments of this invention, the disubstituted carbamates and the hydroxycarboxylates are employed. Non-limiting examples of these catalyst compounds include indenyl zirconium tris(diethylcarbamate), indenyl zirconium tris(trimethylacetate), indenyl zirconium tris(p-toluate), indenyl zirconium tris(benzoate), (1-methylindenyl)zirconium tris (trimethylacetate), (2-methylindenyl) zirconium tris (diethylcarbamate), (methylcyclopentadienyl)zirconium tris (trimethylacetate), cyclopentadienyl tris(trimethylacetate), tetrahydroindenyl zirconium tris(trimethylacetate), and (pentamethyl-cyclopentadienyl)zirconium tris(benzoate). Preferred examples are indenyl zirconium tris(diethylcarbamate), indenylzirconium tris(trimethylacetate), and (methylcyclopentadienyl)zirconium tris(trimethylacetate).

In another embodiment of the invention the additional catalyst compounds are those nitrogen containing heterocyclic ligand complexes, based on bidentate ligands containing pyridine or quinoline moieties, such as those described in WO 96/33202, WO 99/01481, WO 98/42664 and U.S. Pat. No. 5,637,660.

It is within the scope of this invention, in one embodiment, that catalyst compound complexes of $Ni^{2+}$ and $Pd^{2+}$ described in the articles Johnson, et al., "New Pd(II)- and Ni(II)-Based Catalysts for Polymerization of Ethylene and a-Olefins", *J.A.C.S.*, (1995) 117, 6414-6415 and Johnson, et al., "Copolymerization of Ethylene and Propylene with Functionalized Vinyl Monomers by Palladium(II) Catalysts", *J.A.C.S.*, (1996) 118, 267-268, and WO 96/23010, may be combined with the present metal complexes for use in the process of the invention. These complexes can be either dialkyl ether adducts, or alkylated reaction products of the described dihalide complexes that can be activated to a cationic state by the conventional-type cocatalysts or the activators of this invention described below.

Additional suitable catalyst compounds for use in the foregoing mixed catalyst compositions are diimine based ligands containing Group 8 to 10 metal compounds disclosed in PCT publications WO 96/23010 and WO 97/48735 and Gibson, et al., *Chem. Comm.*, (1998) 849-850.

Other catalysts are those Group 5 and 6 metal imido complexes described in EP-A-0 816 384 and U.S. Pat. No. 5,851, 945. In addition, catalysts include bridged bis(arylamido) Group 4 compounds described by D. H. McConville, et al., *Organometallics* (1995) 14, 5478-5480. Other catalysts are described as bis(hydroxy aromatic nitrogen ligands) in U.S. Pat. No. 5,852,146. Other metallocene-type catalysts containing one or more Group 15 atoms include those described in WO 98/46651. Still another metallocene-type catalysts include those multinuclear catalysts as described in WO 99/20665.

It is contemplated in some embodiments, that the catalyst compounds employed in addition to those of the invention described above may be asymmetrically substituted in terms of additional substituents or types of substituents, and/or unbalanced in terms of the number of additional substituents on the π-bonded ligand groups. It is also contemplated that such additional catalysts may include their structural or optical or enantiomeric isomers (meso and racemic isomers) and mixtures thereof, or they may be chiral and/or a bridged catalyst compounds.

In one embodiment of the invention, one or more olefins, preferably one or more $C_{2-30}$ olefins, preferably ethylene and/or propylene are prepolymerized in the presence of the catalyst composition prior to the main polymerization. The prepolymerization can be carried out batchwise or continuously in gas, solution or slurry phase including at elevated pressures. The prepolymerization can take place with any olefin monomer or combination and/or in the presence of any molecular weight controlling agent such as hydrogen. For examples of prepolymerization procedures, see U.S. Pat. Nos. 4,748,221, 4,789,359, 4,923,833, 4,921,825, 5,283,278 and 5,705,578, European publication EP-A-279863, and PCT Publication WO 97/44371. A prepolymerized catalyst composition for purposes of this patent specification and appended claims preferably is a supported catalyst system.

The method for making the catalyst composition generally involves the combining, contacting, blending, and/or mixing of the respective catalyst components, optionally in the presence of the monomer or monomers to be polymerized. Ideally, the contacting is conducted under inert conditions or under polymerization conditions at a temperature in the range of from 0 to 200° C., more preferably from 15 to 190° C., and preferably at pressures from ambient (600 kPa) to 1000 psig (7 MPa). The contacting is desirably performed under an inert gaseous atmosphere, such as nitrogen, however, it is also contemplated that the combination may be performed in the presence of olefin(s), solvents, and hydrogen.

Mixing techniques and equipment contemplated for use in the method of the invention are well known. Mixing techniques may involve any mechanical mixing means, for example shaking, stirring, tumbling, and rolling. Another technique contemplated involves the use of fluidization, for example in a fluid bed reactor vessel where circulated gases provide the mixing.

For supported catalyst compositions, the catalyst composition is substantially dried and/or free flowing. In a preferred embodiment, the various components are contacted in a rotary mixer, tumble mixer, or in a fluidized bed mixing process, under a nitrogen atmosphere, and any liquid diluent is subsequently removed.

Suitable addition polymerization processes wherein the present catalyst compositions may be employed include solution, gas phase, slurry phase, high pressure, or combinations thereof. Particularly preferred is a solution or slurry polymerization of one or more olefins at least one of which is ethylene, 4-methyl-1-pentene, or propylene. The invention is particularly well suited to processes wherein propylene, 1-butene, or 4-methyl-1-pentene is homopolymerized, ethylene and propylene are copolymerized, or ethylene, propylene, or a mixture thereof is copolymerized with one or more monomers selected from the group consisting of 1-octene, 4-methyl-1-pentene, ethylidenenorbornene, 2,4-hexadiene, and 1-butene. The homopolymers of butene-1 and 4-methyl-1-pentene and copolymers thereof, especially with ethylene or propylene are desirably highly isotactic and usefully employed in adhesive formulations.

Other monomers useful in the process of the invention include ethylenically unsaturated monomers, diolefins having 4 to 18 carbon atoms, conjugated or nonconjugated dienes, polyenes, vinyl monomers and cyclic olefins. Nonlimiting monomers useful in the invention include norbornene, isobutylene, vinylbenzocyclobutane, styrenes, alkyl substituted styrene, ethylidene norbornene, isoprene, 1-pentene, dicyclopentadiene and cyclopentene.

Typically, in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. Examples of such processes are disclosed in U.S. Pat. Nos. 4,543,399, 4,588,790, 5,028,670, 5,317,036, 5,352,749, 5,405,922, 5,436,304, 5, 453,471, 5,462,999, 5,616,661 and 5,668,228.

The reactor pressure in a gas phase process may vary from 100 psig (700 kPa) to 500 psig (3500 kPa), preferably in the range of from 200 psig (1400 kPa) to 400 psig (2800 kPa), more preferably in the range of from 250 psig (1700 kPa) to 350 psig (2400 kPa).

The reactor temperature in the gas phase process may vary from 30 to 120° C., preferably from 60 to 115° C., more preferably from 70 to 110° C., and most preferably from 70 to 95° C.

A slurry polymerization process generally uses pressures in the range of from 100 kPa to 5 MPa, and temperatures in the range of 0 to 120° C. In a slurry polymerization, a suspension of solid, particulate polymer is formed in a liquid polymerization diluent to which monomers and often hydrogen along with catalyst are added. The diluent is intermittently or continuously removed from the reactor where the volatile components are separated from the polymer and recycled to the reactor. The liquid diluent employed should remain a liquid under the conditions of polymerization and be relatively inert. Preferred diluents are aliphatic or cycloaliphatic hydrocarbons, preferably propane, n-butane, isobutane, pentane, isopentane, hexane, cyclohexane, or a mixture thereof is employed. Examples of suitable slurry polymerization processes for use herein are disclosed in U.S. Pat. Nos. 3,248,179 and 4,613,484.

Examples of solution processes that are suitably employed with the catalyst compositions of the present invention are described in U.S. Pat. Nos. 4,271,060, 5,001,205, 5,236,998 and 5,589,555. Highly preferably, the solution process is an ethylene polymerization or an ethylene/propylene copolymerization operated in a continuous or semi-continuous manner with high ethylene conversion, preferably greater than 98 percent, more preferably greater than 99.5 percent ethylene conversion. Typical temperatures for solution polymerizations are from 70 to 150° C., more preferably from 100 to 130° C.

Regardless of the process conditions employed (gas phase, slurry or solution phase) in order to achieve the benefits of the present invention, the present polymerization is desirably conducted at a temperature greater than or equal to 100° C., more preferably greater than or equal to 110° C., and most preferably greater than or equal to 115° C.

Polymer Properties

The polymers produced by the process of the invention can be used in a wide variety of products and end-use applications. The polymers produced by the process of the invention include high density polyethylenes, low density polyethylene, linear, low density polyethylene (ethylene/α-olefin copolymers), polypropylene, ethylene/propylene copolymers, and ethylene/propylene/diene terpolymers. Especially preferred polymers are propylene/ethylene- or propylene/ethylene/diene interpolymers containing 65 percent or more, preferably 85 percent or more polymerized propylene and substantially isotactic propylene segments.

The ethylene homopolymers and high ethylene content copolymers formed by the present process preferably have a density in the range of from 0.85 g/cc to 0.97 g/cc, more preferably in the range of from 0.86 g/cc to 0.92 g/cc. Desirably they additionally have melt index ($I_2$) determined according to ASTM D-1238, Condition E, from 1 to 100 dg/min, preferably from 2 to 10 dg/min. Propylene/ethylene copolymers prepared according to the present process desirably have a $\Delta H_f$ (j/g) from 25 to 55, preferably from 29-52. Highly desirably polymers prepared according to the present invention are propylene/ethylene copolymers containing 85 to 95 percent, preferably 87 to 93 percent polymerized propylene, a density from 0.860 to 0.885, and a melt flow rate (MFR) determined according to ASTM D-1238, Condition L, from 10 to 500, preferably 10 to 100. Typically, the polymers produced by the process of the invention have a molecular weight distribution or polydispersity index (Mw/Mn or PDI) from 2.0 to 15.0, preferably from 2.0 to 10.0.

"Broad polydispersity", "broad molecular weight distribution", "broad MWD" and similar terms mean a PDI greater than or equal to 3.0, preferably from 3.0 to 8.0. Polymers for use in fiber and extrusion coating applications typically have a relatively broad polydispersity. Catalysts comprising a complex according to formula 1a are especially adapted for preparing such propylene/ethylene interpolymers having a broad molecular weight distribution for this end use.

"Narrow polydispersity", "narrow molecular weight distribution", "narrow MWD" and similar terms mean a PDI of less than 3.0, preferably from 2.0 to 2.7. Polymers for use in adhesive applications preferentially have a narrower polydispersity. Catalysts comprising a complex according to formula 1b are especially adapted for preparing such narrow molecular weight distribution propylene/ethylene interpolymers for this end use.

A suitable technique for determining molecular weight distribution of the polymers is gel permeation chromatography (GPC) using a Polymer Laboratories PL-GPC-220 high temperature chromatographic unit equipped with four linear mixed bed columns (Polymer Laboratories (20-μm particle size)). The oven temperature is set at 160° C. with the autosampler hot zone at 160° C. and the warm zone at 145° C. The solvent is 1,2,4-trichlorobenzene containing 200 ppm 2,6-di-t-butyl-4-methylphenol. The flow rate is 1.0 milliliter/minute and the injection size is 100 microliters. About 0.2 percent solutions of the samples are prepared for injection by dissolving the sample in nitrogen purged 1,2,4-trichlorobenzene containing 200 ppm 2,6-di-t-butyl-4-methylphenol for 2.5 hours at 160° C. with gentle mixing The molecular weight is determined by using ten narrow molecular weight distribution polystyrene standards (from Polymer Laboratories, EasiCal PS1 ranging from 580 to 7,500,000 g/mole) in conjunction with their elution volumes. The equivalent polypropylene molecular weights are determined by using appropriate Mark-Houwink coefficients for polypropylene (*J. Appl. Polym. Sci.*, 29, 3763-3782 (1984)) and polystyrene (*Macromolecules*, 4, 507 (1971)) in the Mark-Houwink equation: {N}=KMa,
where $K_{pp}=1.90\times10^{-4}$, $a_{pp}=0.725$ and $K_{ps}=1.26\times10^{-4}$, $a_{ps}=0.702$.

One suitable technique for measuring polymer thermal properties is by means of differential scanning calorimetry (DSC). General principles of DSC measurements and applications of DSC to studying crystalline polymers are described in standard texts such as, E. A. Turi, ed., "Thermal Characterization of Polymeric Materials", Academic Press, (1981). A suitable technique for conducting DSC analyses is by using a model Q1000 DSC DSC device from TA Instruments, Inc. To calibrate the instrument, first a baseline is obtained by running the DSC from −90° C. to 290° C. without any sample in the aluminum DSC pan. Then 7 grams of a fresh indium sample is analyzed by heating the sample to 180° C., cooling the sample to 140° C. at a cooling rate of 10° C./min followed by keeping the sample isothermally at 140° C. for 1 minute, followed by heating the sample from 140° C. to 180° C. at a heating rate of 10° C./min. The heat of fusion and the onset of melting of the indium sample are determined and checked to be within 0.5° C. from 156.6° C. for the onset of melting and within 0.5 J/g from 28.71 J/g for the heat of fusion. Then deionized water is analyzed by cooling a small drop of fresh sample in the DSC pan from 25° C. to −30° C. at a cooling rate of 10° C./min. The sample is retained at −30° C. for 2 minutes and heated to 30° C. at a heating rate of 10° C./min. The onset of melting is determined and checked to be within 0.5° C. from 0° C.

The samples are prepared by pressing the polymer into a thin film at a temperature of 190° C. About 5 to 8 rag of film sample is weighed and placed in the DSC pan. The lid is crimped on the pan to ensure a closed atmosphere. The sample pan is placed in the DSC cell and then heated at a rate of about 100° C./min to a temperature of about 30° C. above the melt temperature. The sample is kept at this temperature for about 3 minutes then cooled at a rate of 10° C./min to −40° C., and held at that temperature for 3 minutes. Next the sample is again heated at a rate of 10° C./min until melting is complete. The resulting enthalpy curves are analyzed for peak melt temperature, onset and peak crystallization temperatures, heat of fusion, and heat of crystallization.

The present interpolymers of propylene with ethylene and optionally $C_{4-20}$ α-olefins have a relatively broad melting point as evidenced by the DSC heating curve. It is believed that this may be due to the unique distribution of ethylene polymer sequences within the polymer chains. As a consequence of the foregoing fact, melting point data, Tm, are not generally reported herein or utilized in describing polymer properties. Crystallinity is determined based on $\Delta H_f$ measurements, with percent crystallinity determined by the formula: $\Delta H_f/165(j/g)\times100$. Generally, a relatively narrow melting peak is observed for propylene/ethylene interpolymers prepared using a metallocene catalyst whereas the polymers according to the present invention possess a relatively broad melting point curve. Polymers having a broadened melting point have been found to be highly useful in applications requiring a combination of elasticity and high temperature performance, such as elastomeric fibers or adhesives, for example.

One characteristic in the DSC curve of propylene/ethylene polymers possessing a relatively broad melting point is that the $T_{me}$, the temperature at which the melting ends, remains essentially the same and $T_{max}$, the peak melting temperature, decreases as the amount of ethylene in the copolymer is increased. An additional feature of such polymers is that the skewness of the TREF curve is generally greater than −1.60, more preferably greater than −1.00.

The determination of crystallizable sequence length distribution in a copolymer can be measured by the technique of temperature-rising elution fractionation (TREF), as disclosed by L. Wild, et al., *Journal of Polymer Science: Polymer. Physics Ed.*, 20, 441 (1982), Hazlitt, *Journal of Applied Polymer Science: Appl. Polym. Symp.*, 45, 25 (1990), and elsewhere. One version of this technique, analytical temperature-rising elution fractionation (ATREF), is not concerned with the actual isolation of fractions, but with more accurately determining the weight distribution of fractions, and is especially suited for use with small sample sizes.

While TREF and ATREF were originally applied to the analysis of copolymers of ethylene and higher α-olefins, they can also be adapted for the analysis of copolymers of propylene with ethylene (or higher α-olefins). The analysis of copolymers of propylene may require use of higher temperatures for the dissolution and crystallization of pure, isotactic polypropylene, but most of the copolymerization products of interest elute at similar temperatures as observed for copolymers of ethylene. The following table summarizes the conditions used for the analysis of propylene/ethylene copolymers.

| Parameter | Explanation |
| --- | --- |
| Column type and size | Stainless steel shot with 1.5 cc interstitial volume |
| Mass detector | Single beam infrared detector at 2920 cm$^{-1}$ |
| Injection temperature | 150° C. |
| Temperature control device | GC oven |
| Solvent | 1,2,4-trichlorobenzene |
| Concentration | 0.1 to 0.3 percent (%) (weight/weight) |
| Cooling Rate 1 | 140° C. to 120° C. @ −6.0° C./min. |
| Cooling Rate 2 | 120° C. to 44.5° C. @ −0.1° C./min. |
| Cooling Rate 3 | 44.5° C. to 20° C. @ −0.3° C./min. |
| Heating Rate | 20° C. to 140° C. @ 1.8° C./min. |
| Data acquisition rate | 12/min. |

The data obtained from TREF or ATREF analysis are expressed as a normalized plot of polymer weight fraction as a function of elution temperature. The separation mechanism is analogous to that of copolymers of ethylene, whereby the molar content of the crystallizable component (ethylene) is the primary factor determining the elution temperature. In the case of copolymers of propylene, the molar content of isotactic propylene units primarily determines the elution temperature.

The TREF or ATREF curve of a metallocene-catalyzed homogeneous propylene/ethylene copolymer is characterized by a gradual tailing at lower elution temperatures compared to the sharpness or steepness of the curve at higher elution temperatures. A statistic that reflects this type of asymmetry is skewness. The skewness index, $S_{ix}$, determined by the following formula, may be employed as a measure of this asymmetry.

$$S_{ix} = \frac{\sqrt[3]{\sum w_i * (T_i - T_{Max})^3}}{\sqrt{\sum w_i * (T_i - T_{Max})^2}}$$

The value, $T_{max}$, is defined as the temperature of the largest weight fraction eluting between 50 and 90° C. in the TREF curve. $T_i$ and $w_i$ are the elution temperature and weight fraction respectively of an arbitrary, $i^{th}$ fraction in the TREF distribution. The distributions are normalized (the sum of the $w_i$ equals 100 percent) with respect to the total area of the curve eluting above 30° C. Thus, the index reflects only the properties of the crystallized polymer and any influence due to uncrystallized polymer (polymer still in solution at or below 30° C.) is omitted from the calculation.

The polymers according to the invention having a relatively broad melting point on the DSC curve desirably are characterized by a skewness index greater than −1.6, more preferably greater than −1.2.

Polymer tacticity, propylene content, regio-errors and other properties are determined by standard NMR techniques. Tacticities (mm) or (rr) are calculated based on meso- or regio-triads, and may be expressed as ratios less than one or as percents. Propylene isotacticity at the triad level (mm) is determined from the integrals of the mm triad (22.70-21.28 ppm), the mr triad (21.28-20.67 ppm) and the rr triad (20.67-19.74). The mm isotacticity is determined by dividing the intensity of the mm triad by the sum of the mm, mr, and rr triads. For ethylene containing interpolymers the mr region is corrected by subtracting the 37.5-39 ppm peak integral. For copolymers with other monomers that produce peaks in the regions of the mm, mw, and rr triads, the integrals for these regions are similarly corrected by subtracting the intensity of the interfering peak using standard NMR techniques, once the peaks have been identified. This can be accomplished, for example, by analysis of a series of copolymers of various levels of monomer incorporation, by literature assignments, by isotopic labeling, or other means which are known in the art.

The $^{13}$C NMR peaks corresponding to a regio-error at about 14.6 and about 15.7 ppm are the result of 2,1-insertion errors of propylene units into the growing polymer chain. These peaks are of about equal intensity, and they represent from 0.01-7, preferably 0.01 to 2 mole percent of the propylene insertions into the homopolymer or copolymer chain. Regio-errors are calculated as one half of the sum of the two of methyls showing up at 14.6 and 15.7 ppm, divided by the total methyls at 14-22 ppm. Because the polymers of the invention are able to achieve low molecular weights at reduced reactor temperatures, regio-errors resulting from higher polymerization temperatures are generally reduced and the polymers possess a unique combination of low molecular weight with high crystallinity and a broadened melting point.

Specific Embodiments

The following specific embodiments of the invention and combinations thereof are especially desirable and hereby delineated in order to provide detailed disclosure for the appended claims.

1. A metal complex corresponding to the formula:

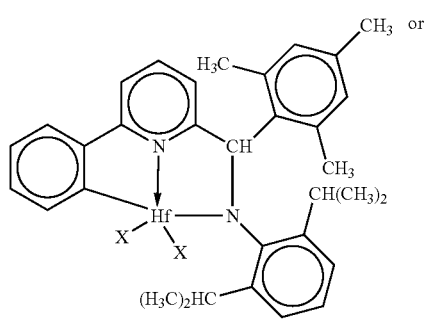

(Ia)

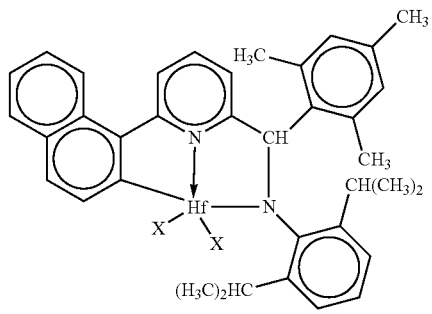

(Ib)

wherein, X is an anionic ligand group, preferably alkyl or alkaryl, more preferably methyl or benzyl; and covalent bonds are represented by lines and coordination interactions are represented by arrows.

2. A metal complex according to embodiment 1 wherein X each occurrence is chloro, methyl, n-butyl, benzyl, or tri(methyl)silylmethyl.

3. An addition polymerization process wherein one or more olefin monomers are contacted with a catalyst composition under polymerization conditions, characterized in that the catalyst composition comprises a metal complex according to embodiment 1 and a cocatalyst.

4. A process according to embodiment 3 which is a solution polymerization process.

5. A process according to embodiment 4 wherein propylene and ethylene are copolymerized, or propylene, ethylene, and one or more monomers selected from the group consisting of 1-octene, 4-methyl-1-pentene, ethylidene norbornene, 2,4-hexadiene, and 1-butene are copolymerized at a temperature from 100 to 130° C., a pressure from 100 kPa to 10 MPa, and a hydrogen partial pressure from 25 to 500 kPa.

6. A process wherein propylene and ethylene are copolymerized at a temperature from 100 to 130° C., a pressure from 100 kPa to 10 MPa, and a propylene/hydrogen flow ratio (g propylene/hr:g H$_2$/hr) from 5000 to 50,000 in the presence of a catalyst comprising a Group 4 metal to prepare a propylene/ethylene copolymer having a Mw from 50,000 to 150,000, a Mw/Mn from 2.0 to 10, a density from 0.860 to 0.885, an ethylene content from 5 to 15 percent, an isotacticity (percent mm) of at least 90, and a B-value from 1.03 to 1.09.

7. A process according to embodiment 6 wherein propylene and ethylene are copolymerized at a temperature from 100 to 130° C., a pressure from 100 kPa to 10 MPa, and a propylene/hydrogen flow ratio (g propylene/hr:g H$_2$/hr) from 5000 to 50,000 to prepare a propylene/ethylene copolymer having a Mw from 50,000 to 150,000, a Mw/Mn from 2.0 to 10, a density from 0.860 to 0.885, an ethylene content from 5 to 15 percent, an isotacticity (percent mm) of at least 90, $\Delta H_f$ from 25 to 55 j/g; and a B-value from 1.03 to 1.09.

8. A process according to embodiment 6 wherein propylene and ethylene are copolymerized at a temperature from 100 to 105° C., a pressure from 100kPa to 10 MPa, and a propylene/hydrogen flow ratio (g propylene/hr:g H$_2$/hr) from 5000 to 50,000 to prepare a propylene/ethylene copolymer having a Mw from 50,000 to 100,000, a Mw/Mn from 2.0 to 3.0, a density from 0.860 to 0.885, an ethylene content from 7 to 12 percent, an isotacticity (percent mm) of at least 93, and a B-value from 1.04 to 1.09.

9. A process according to embodiment 6 wherein propylene and ethylene are copolymerized at a temperature from 100 to 105° C., a pressure from 100 kPa to 10 MPa, and a propylene/hydrogen flow ratio (g propylene/hr:g $H_2$/hr) from 5000 to 50,000 to prepare a propylene/ethylene copolymer having a Mw from 50,000 to 100,000, a Mw/Mn from 2.0 to 3.0, a density from 0.860 to 0.885, an ethylene content from 7 to 12 percent, an isotacticity (percent mm) of at least 93, $\Delta H_f$ from 25 to 55 j/g; and a B-value from 1.04 to 1.09.

10. A propylene/ethylene copolymer having a Mw from 50,000 to 150,000, a Mw/Mn from 2.0 to 10, a density from 0.860 to 0.885, an ethylene content from 5 to 15 percent, an isotacticity (percent mm) of at least 90, and a B-value from 1.03 to 1.09.

11. A propylene/ethylene copolymer having a Mw from 50,000 to 150,000, a Mw/Mn from 2.0 to 10, a density from 0.860 to 0.885, an ethylene content from 5 to 15 percent, an isotacticity (percent mm) of at least 90, $\Delta H_f$ from 25 to 55 j/g; and a B-value from 1.03 to 1.09.

12. A propylene/ethylene copolymer having a Mw from 50,000 to 150,000, a Mw/Mn from 2.0 to 3.0, a density from 0.860 to 0.885, an ethylene content from 7 to 12 percent, an isotacticity (percent mm) of at least 93, and a B-value from 1.04 to 1.09.

13. A propylene/ethylene copolymer having a Mw from 50,000 to 150,000, a Mw/Mn from 2.0 to 3.0, a density from 0.860 to 0.885, an ethylene content from 7 to 12 percent, an isotacticity (percent mm) of at least 93, $\Delta H_f$ from 25 to 55 j/g; and a B-value from 1.04 to 1.09.

14. A propylene/ethylene copolymer having a Mw from 50,000 to 150,000; a Mw/Mn from 2.0 to 10; a density from 0.860 to 0.885; an ethylene content from 7 to 12 percent; an isotacticity (percent mm) of at least 93; $\Delta H_f$ from 25 to 55 j/g; and a B-value from 1.03 to 1.09.

15. A propylene/ethylene copolymer having a Mw from 50,000 to 150,000; a Mw/Mn from 2.0 to 10; a density from 0.860 to 0.885; an ethylene content from 7 to 12 percent; an isotacticity (percent mm) of at least 93; $\Delta H_f$ from 29 to 52 j/g; and a B-value from 1.04 to 1.09.

EXAMPLES

The invention is further illustrated by the following Examples that should not be regarded as limiting of the present invention. The skilled artisan will appreciate that the invention disclosed herein may be practiced in the absence of any component which has not been specifically disclosed. The term "overnight", if used, refers to a time of approximately 16-18 hours, the term "room temperature", refers to a temperature of 20-25° C., and the term "mixed alkanes" refers to a commercially obtained mixture of $C_{6-9}$ aliphatic hydrocarbons available under the trade designation Isopar E®, from Exxon Mobil Chemicals Inc. In the event the name of a compound herein does not conform to the structural representation thereof, the structural representation shall control. The synthesis of all metal complexes and the preparation of all screening experiments were carried out in a dry nitrogen atmosphere using dry box techniques. All solvents used were HPLC grade and were dried before their use.

Example 1 Hafnium, [N-[2,6-bis(1-methylethyl)phenyl]-α-[2,4,6-trimethylphenyl]-6-(phenyl-κ-$C^2$)-2-pyridinemethaneaminato(2-),$N^1$,κ$N^2$]dichloride

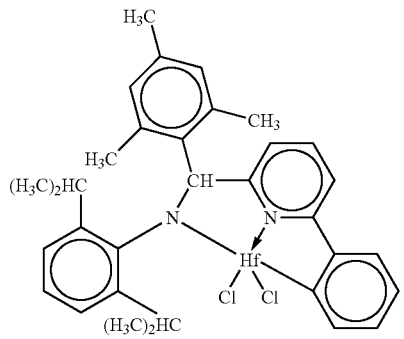

a) 2-Formyl-6-bromopyridine This compound is synthesized substantially according to literature procedures (*Tetrahedron. Letters*, 2001, 42, 4841).

b) 6-Bromo-2-(2,6-diisopropylphenyl)iminopyridine) A dry, 500 mL 3-neck round bottom flask is charged with a solution of 2-formyl-6-bromopyridine (72.1 g, 383 mmol) and 2,6-diisopropylaniline (72.5 g, 383 mmol) in 500 mL of anhydrous toluene containing 0.3 nm molecular sieves (6 g) and 80 mg of p-toluene sulfonic acid. The reactor is equipped with a condenser, an overhead mechanical stirrer and a thermocouple well. The mixture is heated to 70° C. under $N_2$ for 12 h. After filtration and removal of the volatiles under reduced pressure, a brown oil is isolated. Yield is 109 g, 81.9 percent.

c) 6-(phenyl)-2-[(2,6-diisopropylphenyl)imino]pyridine Phenylboronic acid (316 mmol) and $Na_2CO_3$ (792 mmol) are dissolved into 200 mL of degassed 1:1 $H_2O$/ethanol. This solution is added to a toluene solution (500 mL) of 6-bromo-2-(2,6-diisopropylphenyl)iminopyridine (109 g, 316 mmol). Inside of a dry box 1 g (0.86 mmol) of tetrakis(triphenylphosphine)palladium(0) is dissolved in 50 mL of degassed toluene. The solution is removed from the dry box and charged into the $N_2$ purged reactor. The biphasic solution is vigorously stirred and heated to 70° C. for 4-12 h. After cooling to room temperature, the organic phase is separated, the aqueous layer is washed with toluene (3×75 mL), and the combined organic extracts are washed with $H_20$ (3×200 mL) and dried over $MgSO_4$. After removing the volatiles under reduced pressure, the resultant light yellow oil is purified via recrystallization from methanol to give a yellow solid. Yield is 109 g, 87.2 percent; mp 142-144° C.

d) pyridinemethanamine,N-[2,6-bis(1-methylethyl)phenyl]-α-[2,4,6-trimethyl)phenyl]-6-(1-phenyl) The imine, 6-(phenyl)-2-[(2,6-diisopropylphenyl)imino]-pyridine (1.0 g, 2.9 mmol) is magnetically stirred as a slurry in 60-70 mL of dry ether under a nitrogen atmosphere at −40° C. An ether solution of mesityl lithium (0.55 g, 4.3 mmol in 25 mL dry ether) is added slowly using a syringe over a period of 4-5 minutes. After the addition is complete, the mixture is warmed to 0° C. and continued until analysis by thin layer chromatography indicates substantial completion has occurred. The reaction is quenched through slow addition of 1N aqueous $NH_4Cl$ (10 mL). The mixture is diluted with more ether, then washed 2 times with brine, then dried over $Na_2SO_4$, filtered and stripped of solvent under reduced pressure. The crude product obtained is a yellow oil (1.18 g; 88 percent) and used without further purification.

e) Hafnium, [N-[2,6-bis(1-methylethyl)phenyl]-α-[2,4,6-trimethylphenyl]-6-(1-phenyl-κ-$C^2$)-2-pyridinemethanaminato(2-)-κ$N^1$,κ$N^2$]dichloride A glass jar is charged with 1.77 mmol of the ligand from step a) above dissolved in 30 mL hexane. To this solution is added 1.77 mmol of n-BuLi (2.5 M solution in hexanes) by syringe. This solution is stirred for 0.5 hour, the hexane removed, toluene added, and then 1.77 mmol of solid $HfCl_4$ is added. The jar is capped with an air-cooled reflux condenser and the mixture is heated at reflux for about 1 hour. The product was not isolated.

Example 2 Hafnium, [N-[2,6-bis(1-methylethyl)phenyl]-α-[2,4,6-trimethylphenyl]-6-(phenyl-κ-$C^2$)-2-pyridinemethaneaminato(2-), $N^1$,κ$N^2$]dimethyl

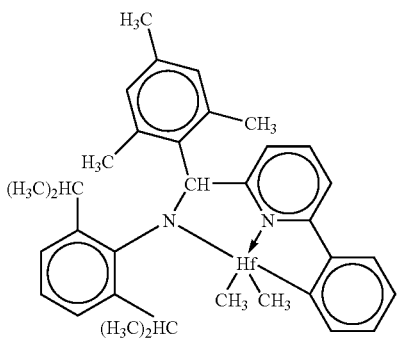

The reaction mixture from Example 1, step e) is cooled and 5.31 mmol of MeMgBr (3 equivalents, 3.0 M solution in diethyl ether) is added by syringe and the resulting mixture is stirred overnight at ambient temperature. Solvent (toluene, hexanes and diethyl ether) is removed from the reaction mixture under reduced pressure. Toluene (30 ml) is added to the residue and the mixture filtered, and the residue is washed with additional toluene (30 mL). Solvent is removed under reduced pressure from the mixture and hexane is added then removed by vacuum. Hexane is again added, the resulting slurry is filtered and the product is washed with pentane to give the desired product as a pale yellow powder. Yield is 45 percent.

$^1$H NMR $C_6D_6$): δ 8.4 (d, 1H), 7.4-7.6 (multiplets, 2H), 6.8-7.4 (multiplets, 6H), 6.6 (multiplets, 3H), 6.4 (d, 1H), 3.8 (septet, 1H), 3.3 (septet, 1H), 2.1 (s, 3H), 2.0 (s, 3H), 1.8 (s, 3H), 1.4 (d, 3H), 1.4 (d, 3H), 1.2 (d, 3H), 1.0 (s, 3H), 0.70 (s, 3H), 0.4 (d, 3H).

Example 3 Hafnium, [N-[2,6-bis(1-methylethyl)phenyl]-α-[2,4,6-trimethylphenyl]-6-(1-naphthanlenyl-κ-$C^2$)-2-pyridinemethanaminato (2-)-κ$N^1$,κ$N^2$] dichloride

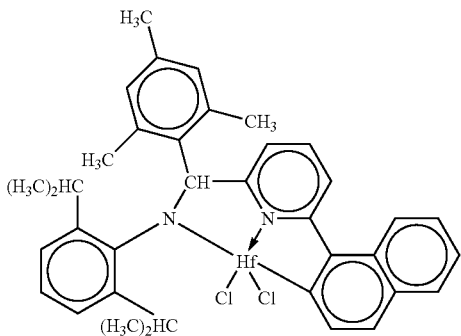

a) 6-Naphthyl-2-[(2,6-diisopropylphenyl)imino]pyridine Naphthylboronic acid (54.5 g, 316 mmol) and $Na_2CO_3$ (83.9 g, 792 mmol) are dissolved into 200 mL of degassed 1:1 $H_2O$/ethanol. This solution is added to a toluene solution (500 mL) of 6-bromo-2-(2,6-diisopropylphenyl)iminopyridine (Ex. 1, step b), 109 g, 316 mmol). Inside of a dry box 1 g (0.86 mmol) of tetrakis(triphenylphosphine)palladium(0) is dissolved in 50 mL of degassed toluene. The solution is removed from the dry box and charged into the $N_2$ purged reactor. The biphasic solution is vigorously stirred and heated to 70° C. for 4-12 h. After cooling to room temperature, the organic phase is separated, the aqueous layer is washed with toluene (3×75 mL), and the combined organic extracts are washed with $H_2O$ (3×200 mL) and dried over $MgSO_4$. After removing the volatiles under reduced pressure, the resultant light yellow oil is purified via recrystallization from methanol to give a yellow solid. Yield is 109 g, 87.2 percent; mp 142-144° C.

b) 2-pyridinemethanamine,N-[2,6-bis(1-methylethyl)phenyl]-α-[2,4,6-trimethyl)phenyl]-6-(1-naphthanlenyl) The imine, 6-Naphthyl-2-[(2,6-diisopropylphenyl)imino]pyridine (2.0 g, 5 mmol) is magnetically stirred as a slurry in 60-70 mL of dry ether under a nitrogen atmosphere at ambient temperature. An ether solution of mesityl lithium (1.28 g, 10 mmol in about 25 mL dry ether) is added slowly using a syringe over a period of 4-5 minutes. The reaction mixture is stirred overnight, then quenched by the careful, slow addition of 1N $NH_4Cl$ (10 mL). The mixture is diluted with more ether, washed 2 times with brine, then dried over $Na_2SO_4$, filtered and stripped of solvent under reduced pressure. The crude product obtained is a brown solid (2.44 g, 95 percent) and used without further purification.

c) Hafnium, [N-[2,6-bis(1-methylethyl)phenyl]-α-[2,4,6-trimethylphenyl]-6-(1-naphthanlenyl-κ-$C^2$)-2-pyridinemethanaminato(2-)-κ$N^1$, κ$N^2$]dichloride A glass jar is charged with 4.76 mmol of the ligand from step b) dissolved in 30 mL toluene. To this solution is added 4.76 mmol of n-BuLi (2.5 M solution in hexanes) by syringe. This solution is stirred for 0.5 hour. Toluene is removed, hexane added and the resulting brown solid washed with hexane. The resulting brown solid is redissolved in toluene and 3.2 mmol of solid $HfCl_4$ is added. The jar is capped with an air-cooled reflux condenser and the mixture is heated at reflux for about 1 hour.

Example 4 Hafnium, [N-[2,6-bis(1-methylethyl)phenyl]-α-[2,4,6-trimethylphenyl]-6-(1-naphthanlenyl-κ-$C^2$)-2-pyridinemethanaminato(2-)-κ$N^1$,κ$N^2$] dimethyl

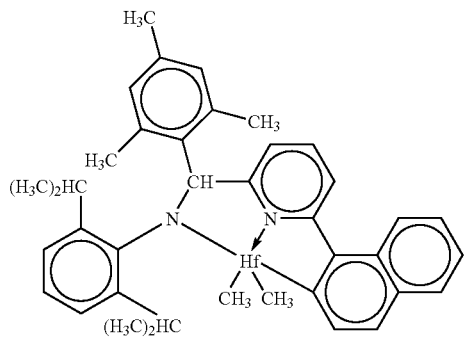

To the cooled reaction mixture of example 3, step c), 11.2 mmol of MeMgBr (3.5 equivalents, 3.0 M solution in diethyl ether) is added by syringe and the resulting mixture stirred overnight at ambient temperature. Solvent (toluene, hexanes and diethyl ether) is removed from the reaction mixture under reduced pressure. Toluene (30 mL) is added to the residue and the mixture filtered, and the residue (magnesium salts) is washed with additional toluene (30 mL). Solvent is removed under reduced pressure from the combined toluene solution and hexane is added, then removed under reduced pressure. Hexane is again added and the resulting slurry is filtered. The resulting solid material is dissolved in benzene, refiltered, dried under reduced pressure, and washed with pentane to give the desired product as a bright yellow powder Yield is 56 percent.

$^1$H NMR (C$_6$D$_6$): δ 8.6 (d, 1H), 8.25 (d, 1H), 7.8 (d, 1H), 7.7 (m, 1H), 7.5 (d, 1H), 7.3 (m, 2H), 7.2 (multiplets, 2H), 7.1 (m, 1H), 6.8 (t, 1H), 6.5-6.7 (multiplets, 3H), 6.4 (d, 1H), 3.8 (septet, 1H), 3.4 (septet, 1H), 2.1 (s, 3H), 2.0 (s, 3H), 1.8 (s, 3H), 1.4 (d, 3H), 1.3 (d, 3H), 1.2 (d, 3H), 1.1 (s, 3H), 0.70 (s, 3H), 0.4 (d, 3H).

Comparative A Hafnium, [N-[2,6-bis(1-methylethyl) phenyl]-α-[2-(2-propyl)phenyl]-6-(1-naphthanlenyl-κ-C$^2$)-2-pyridinemethanaminato(2-)-κN$^1$N, κN$^2$] dimethyl

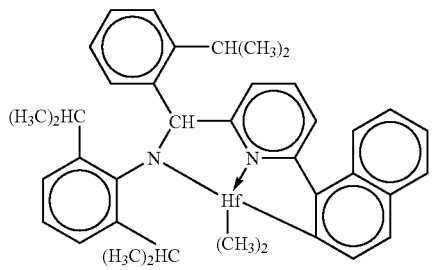

a) 2-[N-(2,6-diisopropylphenylamino)-o-isopropylphenylmethyl]-6-(1-naphthyl)-pyridine. The imine, 6-(1-naphthyl)-2-[(2,6-diisopropylphenyl)imino]pyridine of Ex. 1, step c) (2.20 g, 5.6 mmol) is magnetically stirred as a slurry in 60-70 mL of dry ether under a nitrogen atmosphere. An ether solution of 2-isopropylphenyl lithium (1.21 g, 9.67 mmol in 25 mL dry ether) is added slowly using a syringe over a period of 4-5 min. After the addition is complete, a small sample is removed, quenched with 1N NH$_4$Cl and the organic layer analyzed by high pressure liquid chromatography (HPLC) to check for complete consumption of starting material. The remainder of the reaction is quenched by the careful, slow addition of 1N NH$_4$Cl (10 mL). The mixture is diluted with more ether and the organic layer washed twice with brine, dried (Na$_2$SO$_4$), filtered, and stripped of solvent under reduced pressure. The crude product obtained as a thick red oil (2.92 g; theoretical yield=2.87 g) is used without further purification.

b) 2-[N-(2,6-diisopropylphenylamido)-o-isopropylphenyl-methyl]-6-(2-η-1-naphthyl)-pyridylhafnium(IV) dichloride A glass jar is charged with 8.89 mmol of the ligand from step a) dissolved in 30 mL toluene. To this solution is added 8.98 mmol of n-BuLi (2.5 M solution in hexanes) by syringe. This solution is stirred for 1 hour, then 8.89 mmol of solid HfCl$_4$ are added. The jar is capped with an air-cooled reflux condenser and the mixture is heated at reflux for 1 hour.

c) 2-[N-(2,6-diisopropylphenylamido)-o-isopropylphenyl-methyl]-6-(2-η-1-naphthyl)-pyridylhafnium(IV) dimethyl After cooling the reaction mixture from step b), 31.1 mmol of MeMgBr (3.5 equivalents, 3.0 M solution in diethyl ether) are added by syringe and the resulting mixture stirred overnight at ambient temperature. Solvent (toluene, hexanes and diethyl ether) is removed from the reaction mixture using a vacuum system attached to the drybox. Toluene (30 mL) is added to the residue and the mixture filtered, and the residue (magnesium salts) is washed with additional toluene (30 mL). Solvent is removed by vacuum from the combined toluene solution, and hexane is added, then removed by vacuum. Hexane is again added and the resulting slurry is filtered and the product washed with pentane to give the desired product as a yellow powder.

Comparative B Hafnium, [N-[2,6-bis(1-methylethyl) phenyl]-α-[2-(methyl)phenyl]-6-(1-naphthanlenyl-κ-C$^2$)-2-pyridinemethanaminato (2-)-κN$^1$,κN$^2$]dimethyl

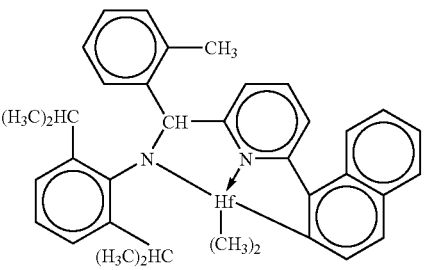

The reaction conditions of Comparative A are substantially repeated excepting that 2-[N-(2,6-diisopropylphenylamino)-o-methylphenylmethyl]-6-(1-naphthyl)pyridine (prepared by reaction of the imine, 6-(1-naphthyl)-2-[(2,6-diisopropylphenyl)imino]pyridine with 2-methylphenyl lithium in diethylether) is reacted with HfCl$_4$.

Batch Reactor Polymerization Conditions

Polymerizations are conducted in a computer controlled, stirred, jacketed 1.8 L stainless steel autoclave solution batch reactor. The bottom of the reactor is fitted with a large orifice bottom dump valve, which empties the reactor contents into a 6 L stainless steel container. The container is vented to a 30 gal. blowdown tank, with both the container and the tank are purged with nitrogen. All chemicals used for polymerization or catalyst makeup are run through purification columns, to remove any impurities. Propylene and solvent, mixed alkanes (Isopar E™ available from Exxon Mobil Chemicals Inc.) or toluene, are passed through 2 columns, the first containing alumina, the second containing a purifying reactant (Q5™ available from Englehardt Corporation). Nitrogen and hydrogen gases are passed through a single column containing Q5™ reactant.

The autoclave is cooled to 25° C. before loading. It was charged with 667 g mixed alkanes, hydrogen (using a calibrated 50 mL shot tank and a differential pressure in the shot tank of 0.41 MPa), followed by 286 g of propylene using a micro-motion flowmeter. The reactor is then brought to 90° C. before addition of catalyst composition.

The metal complex (catalyst) (1.0 μmole) is dissolved in 5 ml toluene. The metal complex and hexane solutions of activator and tertiary component are handled in an inert glovebox, mixed together in a vial, drawn into a syringe and pressure transferred into the catalyst shot tank. This is followed by 3 rinses of toluene, 5 mL each. The cocatalyst used is a long-chain alkyl ammonium borate of approximate stoichiometry equal to methyldi(octadecyl)ammonium tetrakis (pentafluorophenyl)borate (MDB). The tertiary component used is tri(i-propyl)aluminum modified methylalumoxane (PMAO-IP™, available from Akzo Noble, Inc.) in a molar ratio (metal complex:cocatalyst:tertiary component) of 1:1.2:30. The shot tank is pressurized with N$_2$ to 0.6 MPa above the reactor pressure, and the contents are quickly blown into the reactor. Both reaction exotherm and pressure drop are monitored throughout the reaction run time.

After 10 minutes polymerization, the agitator is stopped, the reactor pressure is increased to 3.4 MPa with N$_2$, and the bottom dump valve opened to empty reactor contents to the collection vessel. The contents are poured into trays and placed in a lab hood where the solvent is evaporated overnight. The trays are then transferred to a vacuum oven, where they are heated to 145° C. under vacuum to remove any remaining solvent. After the trays cooled to ambient temperature, the polymers are quantified and analyzed.

Continuous Solution Polymerization Conditions

Continuous polymerizations are carried out in a computer controlled autoclave reactor equipped with an internal stirrer. Purified mixed hexanes solvent, ethylene (where used), hydrogen, and propylene are supplied to a 3.8 L reactor equipped with a jacket for temperature control and an internal thermocouple. The solvent feed to the reactor is measured by a mass-flow controller. A variable speed diaphragm pump controls the solvent flow rate and pressure to the reactor. The propylene feed is measured by a mass flow meter and the flow is controlled by a variable speed diaphragm pump. At the discharge of the pump, a side stream is taken to provide flush flows for the catalyst injection line and the reactor agitator. The remaining solvent is combined with hydrogen and delivered to the reactor. A mass flow controller is used to deliver hydrogen into the reactor as needed. The temperature of the solvent/monomer is controlled by use of a heat exchanger before entering the reactor. This stream enters the bottom of the reactor. The catalyst component solutions are metered using pumps and mass flow meters, and are combined with the catalyst flush solvent. This stream enters the bottom of the reactor, but in a different port than the port used for the monomer stream. The reactor is run liquid-full at 500 psig (3.45 MPa) with vigorous stirring. The process flow enters the bottom and exits the top of the reactor. All exit lines from the reactor are steam traced and insulated. The cocatalyst used is MDB and the tertiary component used is methylalumoxane (MAO-3A™, available from Akzo Noble, Inc.) in a molar ratio (metal complex:cocatalyst:tertiary component) of 1:1.2:30. Polymerization is stopped with the addition of a small amount of water, and other additives and stabilizers can be added without stopping stirring within the reactor. The stream flows through a static mixer and a heat exchanger in order to heat the solvent/polymer mixture. The solvent and unreacted monomers are continuously removed from the exit stream, and the product is recovered by extrusion using a devolatilizing extruder. The extruded strand is cooled under water and chopped into pellets.

The following experimental conditions are employed in producing polypropylene homopolymers. Reactor temperature is set at 100° C., solvent is adjusted to provide 16-18 percent solids, and propylene is regulated to provide 50 percent propylene conversion. The quantity of hydrogen is adjusted to make a product having a melt flow rate (MPR) determined according to ASTM D-1238, condition L (2.16 kg, 230 degrees C.) of 10 using comparative B catalyst. After reaching stable operating conditions, product is collected for 3 hours.

For continuous propylene/ethylene copolymerizations the temperature of the reactor is increased to 105° C. and additional hydrogen is added to the reactor to increase the MFR to a target level of a specified viscosity at 190° C.

Results are reported in Tables 1-5.

TABLE 1

Batch Reactor Propylene Homopolymerization Results:

| Run | Cat. | $\Delta T$ °C. | $\Delta$ Press kPa | Yield g | Efficiency kg poly/gHf | Tc °C. | Tm °C. | Mw | Mw/Mn |
|---|---|---|---|---|---|---|---|---|---|
| A | A | 2.8 | 253 | 52.4 | 294 | 105.5 | 153.2 | 229,000 | 2.22 |
| 1 | Ex. 2 | 5.97 | 384 | 60.6 | 340 | 104.9 | 150.9 | 85,300 | 2.14 |
| 2 | Ex. 4 | 0.68 | 145 | 17.8 | 100 | 107.4 | 157.3 | 68,200 | 2.26 |

TABLE 2

Continuous Propylene Polymerization Conditions

| Run | Cat. | Temp. °C. | Prod. kg/h | Solv. Flow kg/hr | C3 Flow kg/h | H2 Flow sccm | conv % | eff. kg/g Hf |
|---|---|---|---|---|---|---|---|---|
| B | B | 100 | 2.5 | 11.9 | 4.5 | 13.9 | 50.3 | 600 |
| 3 | Ex. 2 | 100 | 2.3 | 11.9 | 4.5 | 14.0 | 50.5 | 546 |
| 4 | Ex. 2 | 122 | 1.9 | 10.6 | 3.2 | 0.7 | 59.3 | 89 |

TABLE 3

Continuous Propylene Homopolymer Properties

| Run | MFR (dg/min) | Density (kg/cm³) | Viscosity (cpoise) | $\Delta$Hf (J/g) | Cryst. (%) | Mw | Mn | PDI |
|---|---|---|---|---|---|---|---|---|
| B | 9.4 | 0.9027 | — | 99.5 | 60.3 | 214,000 | 59,900 | 3.6 |
| 3 | 180.0 | — | — | 98.8 | 59.9 | 107,000 | 13,000 | 8.2 |
| 4 | — | 0.8985 | 3,111 | — | — | — | — | — |

TABLE 4

Continuous Propylene/Ethylene Copolymerization Conditions 105° C.

| Run | Cat. | Prod. kg/h | Solv. Flow kg/hr | C3 Flow kg/h | C2 Flow kg/h | H2 Flow sccm | conv % | efficiency kg/g Hf |
|---|---|---|---|---|---|---|---|---|
| C | A | 2.0 | 10.5 | 3.2 | 0.14 | 57.2 | 61.4 | 243 |
| D | A | 2.1 | " | " | 0.18 | 77.7 | 59.1 | 290 |
| E | A | " | " | " | 0.23 | 117.6 | 60.9 | 275 |
| F | A | " | " | " | 0.18 | 88.4 | 60.2 | 277 |
| G | A | 2.2 | " | " | 0.27 | 143.6 | 60.8 | 313 |
| 5 | Ex. 2 | 2.1 | 10.6 | " | 0.18 | 32.1 | 60.8 | 254 |
| 6 | Ex. 2 | " | " | " | " | 58.7 | 60.1 | 255 |
| 7 | Ex. 4 | " | 10.4 | " | 0.23 | 21.5 | 60.5 | 220 |

TABLE 5

| | | | | | | | | | | | | |
|---|---|---|---|---|---|---|---|---|---|---|---|---|
| | | | Continuous Propylene/Ethylene Copolymer Properties | | | | | | | | | |
| Run | Density (g/cc) | Viscosity (190° C., cP) | Mw (kg/mol) | Mn (kg/mol) | Mw/Mn | Tg (° C.) | Tc, peak (° C.) | ΔHc (J/g) | ΔHf (J/g) | Cryst. (percent) | C2 (percent)* | B |
| C | 0.8869 | 72650 | — | — | — | — | — | — | — | — | 7.6 | 1.07 |
| D | 0.8756 | 64030 | 82.7 | 37.7 | 2.2 | −24.3 | 56.2 | 32.0 | 48.1 | 29.2 | 8.0 | 1.09 |
| E | 0.8770 | 15900 | 55.6 | 24.3 | 2.3 | −24.9 | 57.4 | 32.1 | 47.5 | 28.8 | 8.5 | 1.07 |
| F | 0.8649 | 71150 | 73.2 | 28.8 | 2.5 | −28.0 | 51.1 | 21.1 | 37.3 | 22.6 | 10.5 | 1.09 |
| G | 0.8667 | 14700 | 54.0 | 23.6 | 2.3 | −29.2 | 44.0 | 17.9 | 29.5 | 17.9 | 11.3 | 1.09 |
| 5 | 0.8770 | 65530 | 85.6 | 28.3 | 3.0 | −22.7 | 58.7 | 36.3 | 51.6 | 31.3 | 7.5 | 1.09 |
| 6 | 0.8775 | 17340 | 57.3 | 17.4 | 3.3 | −24.9 | 56.9 | 36.8 | 49.1 | 29.8 | 8.1 | 1.09 |
| 7 | 0.8751 | 70460 | 84.8 | 31.8 | 2.7 | −24.8 | 58.0 | 35.0 | 50.5 | 30.6 | 8.5 | 1.09 |

The invention claimed is:

1. A process wherein propylene and ethylene are copolymerized at a temperature from 100 to 130° C., a pressure from 100 kPa to 10 MPa, and a propylene/hydrogen flow ratio (g propylene/hr:g $H_2$/hr) from 5000 to 50,000 in the presence of a a metal complex corresponding to the formula:

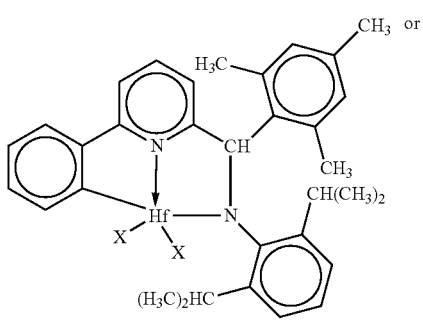

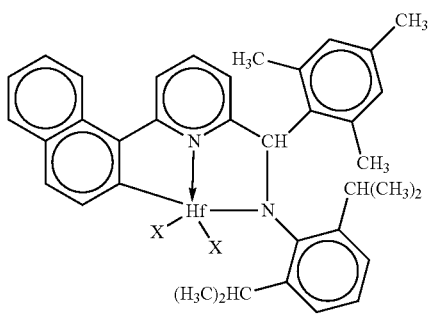

wherein, X is an anionic ligand group; and
covalent bonds are represented by lines and coordination interactions are represented by arrows to prepare a propylene/ethylene copolymer having a Mw from 50,000 to 150,000, a Mw/Mn from 2.0 to 10, a density from 0.860 to 0.885, an ethylene content from 5 to 15 weight percent, an isotacticity (percent mm) of at least 90, and a B-value from 1.03 to 1.09.

2. A process according to claim 1 wherein propylene and ethylene are copolymerized at a temperature from 100 to 130° C., a pressure from 100 kPa to 10 MPa, and a propylene/hydrogen flow ratio (g propylene/hr:g $H_2$/hr) from 5000 to 50,000 to prepare a propylene/ethylene copolymer having a Mw from 50,000 to 150,000, a Mw/Mn from 2.0 to 10, a density from 0.860 to 0.885, an ethylene content from 5 to 15 weight percent, an isotacticity (percent mm) of at least 90, $\Delta H_{fusion}$ from 25 to 55 J/g; and
a B-value from 1.03 to 1.09.

3. A process according to claim 1 wherein propylene and ethylene are copolymerized at a temperature from 100 to 105° C., a pressure from 100 kPa to 10 MPa, and a propylene/hydrogen flow ratio (g propylene/hr:g $H_2$/hr) from 5000 to 50,000 to prepare a propylene/ethylene copolymer having a Mw from 50,000 to 100,000, a Mw/Mn from 2.0 to 3.0, a density from 0.860 to 0.885, an ethylene content from 7 to 12 percent, an isotacticity (percent mm) of at least 93, and a B-value from 1.04 to 1.09.

4. A process according to claim 1 wherein propylene and ethylene are copolymerized at a temperature from 100 to 105° C., a pressure from 100 kPa to 10 MPa, and a propylene/hydrogen flow ratio (g propylene/hr:g $H_2$/hr) from 5000 to 50,000 to prepare a propylene/ethylene copolymer having a Mw from 50,000 to 100,000, a Mw/Mn from 2.0 to 3.0, a density from 0.860 to 0.885, an ethylene content from 7 to 12 percent, an isotacticity (percent mm) of at least 93, $\Delta H_f$ from 25 to 55 j/g; and a B-value from 1.04 to 1.09.

* * * * *